(12) United States Patent
Just

(10) Patent No.: US 11,160,922 B2
(45) Date of Patent: Nov. 2, 2021

(54) SUBCUTANEOUS DELIVERY MECHANISM FOR DRUG DELIVERY DEVICE

(71) Applicant: SENSILE MEDICAL AG, Olten (CH)

(72) Inventor: Manuel Just, Sumiswald (CH)

(73) Assignee: SENSILE MEDICAL AG, Olten (CH)

( * ) Notice: Subject to any disclaimer, the term of this patent is extended or adjusted under 35 U.S.C. 154(b) by 0 days.

(21) Appl. No.: 17/281,271

(22) PCT Filed: Sep. 24, 2019

(86) PCT No.: PCT/EP2019/075765
§ 371 (c)(1),
(2) Date: Mar. 30, 2021

(87) PCT Pub. No.: WO2020/069926
PCT Pub. Date: Apr. 9, 2020

(65) Prior Publication Data
US 2021/0308368 A1 Oct. 7, 2021

(30) Foreign Application Priority Data
Oct. 1, 2018 (EP) ..................................... 18197886

(51) Int. Cl.
*A61M 5/142* (2006.01)
*A61M 5/158* (2006.01)

(52) U.S. Cl.
CPC .................. *A61M 5/14248* (2013.01); *A61M 2005/14252* (2013.01)

(58) Field of Classification Search
CPC .......... A61M 5/14244; A61M 5/14248; A61M 2005/14252; A61M 2005/14284;
(Continued)

(56) References Cited

U.S. PATENT DOCUMENTS 4,448,194 A * 5/1984 DiGiovanni ....... A61B 17/0491
112/80.05
9,554,793 B2 * 1/2017 Lane .................. A61B 17/0482
(Continued)

FOREIGN PATENT DOCUMENTS

EP      3 260 146        12/2017
EP      3574941 A1 *    12/2019    ............ A61M 5/158
(Continued)

OTHER PUBLICATIONS

Written Opinion in International Application No. PCT/EP2019/075765, dated Dec. 6, 2019, pp. 1-5.

*Primary Examiner* — Quynh-Nhu H. Vu
(74) *Attorney, Agent, or Firm* — Saliwanchik, Lloyd & Eisenschenk

(57) ABSTRACT

A subcutaneous delivery mechanism for a drug delivery device (1), comprising a needle (10), a needle holder (12) holding the needle (10), and a needle actuation mechanism (20) configured to actuate in translation the needle holder (12) to move the needle (10) from a retracted position to an extended delivery position. The needle actuation mechanism (20) comprises a first lever (30) pivotally mounted on a first support member (33) and a rotary actuator (22) rotatably mounted on a second support member (43). The first lever (30) is configured to engage the rotary actuator (22). The needle actuation mechanism (20) also comprises a second lever (40) pivotally mounted on the second support member (43) or around a circumferential outer rim (24) of the rotary actuator (22). The first and second levers (30, 40) are coupled to each other such that rotation of the first lever (30) causes rotation of the second lever (40). The second lever (40) is coupled to the needle holder (12) in order to move the needle (10) from the retracted position to the extended delivery position upon rotation of the second lever (40).

12 Claims, 9 Drawing Sheets

(58) Field of Classification Search
CPC .......... A61M 5/158; A61M 2005/1583; A61M 2005/1585; A61M 5/162; A61M 5/20; A61M 5/2033; A61M 2005/206; A61M 2005/3289; A61M 5/3293; A61M 2005/14268; A61M 2005/14533; A61M 60/40

See application file for complete search history.

(56) References Cited

U.S. PATENT DOCUMENTS

| | | | |
|---|---|---|---|
| 10,076,605 B2* | 9/2018 | Marbet | A61M 5/158 |
| 10,632,249 B2 | 4/2020 | Marbet et al. | |
| 2016/0184512 A1* | 6/2016 | Marbet | A61M 5/14248 604/156 |
| 2016/0250422 A1* | 9/2016 | Koch | A61M 5/14248 604/110 |

FOREIGN PATENT DOCUMENTS

| | | |
|---|---|---|
| WO | WO 2015/015379 | 2/2015 |
| WO | WO 2015/032741 | 3/2015 |
| WO | WO 2015/059192 | 4/2015 |

* cited by examiner

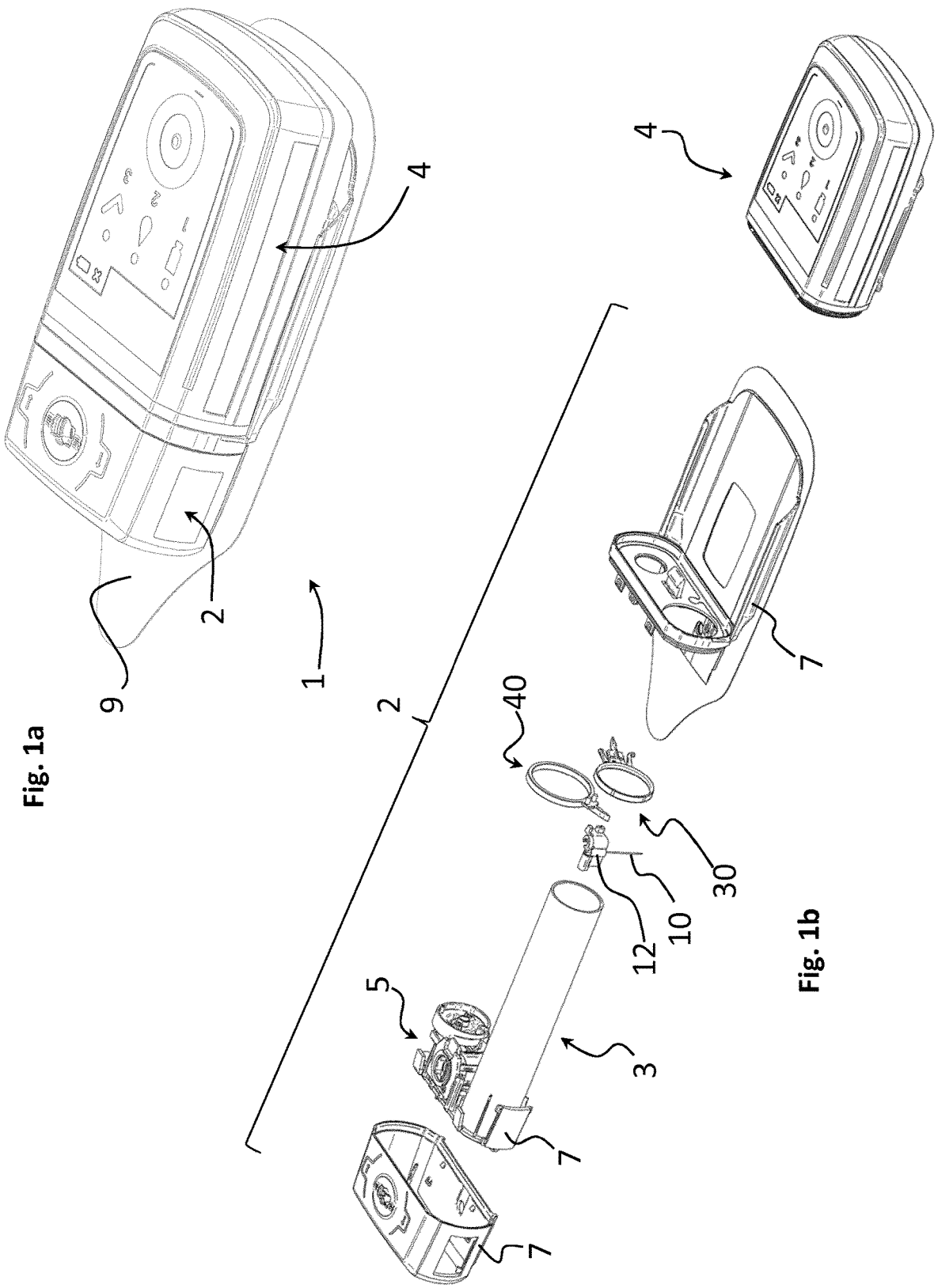

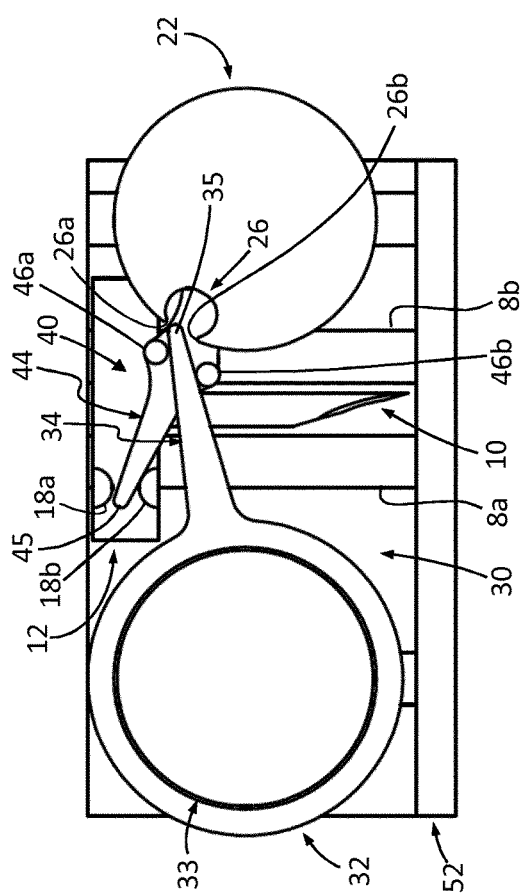
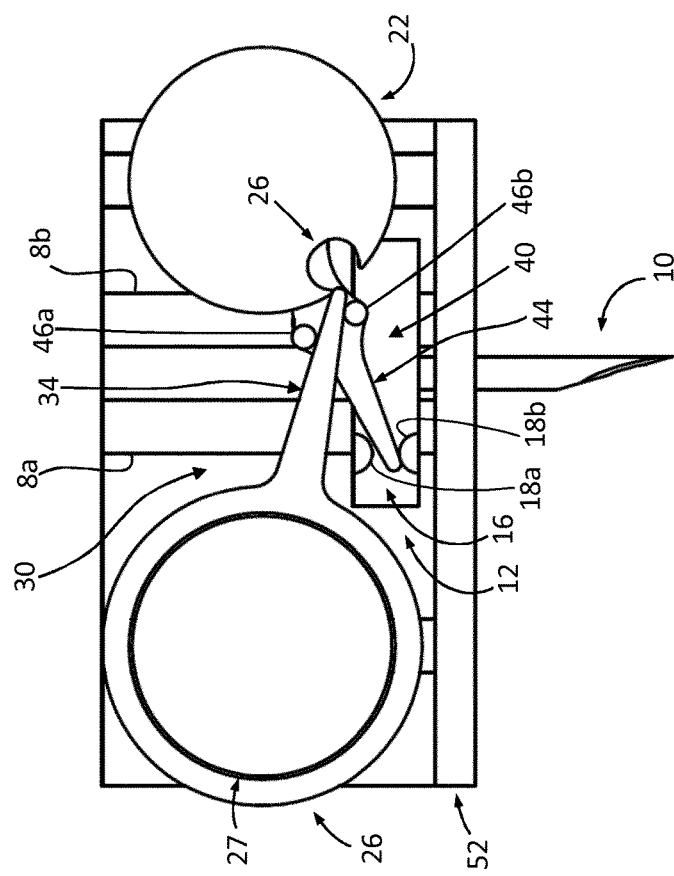
Fig. 3a
Fig. 3b

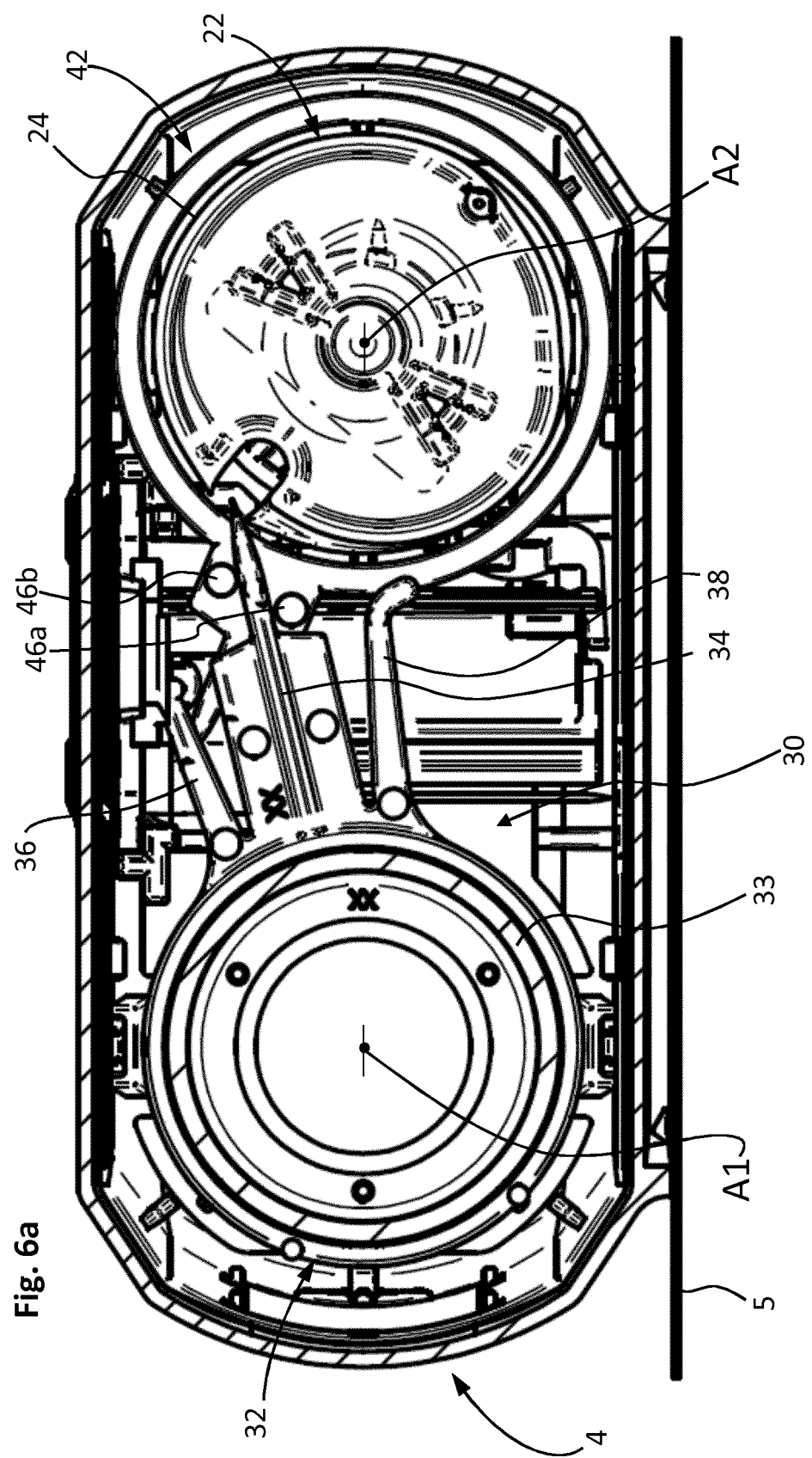

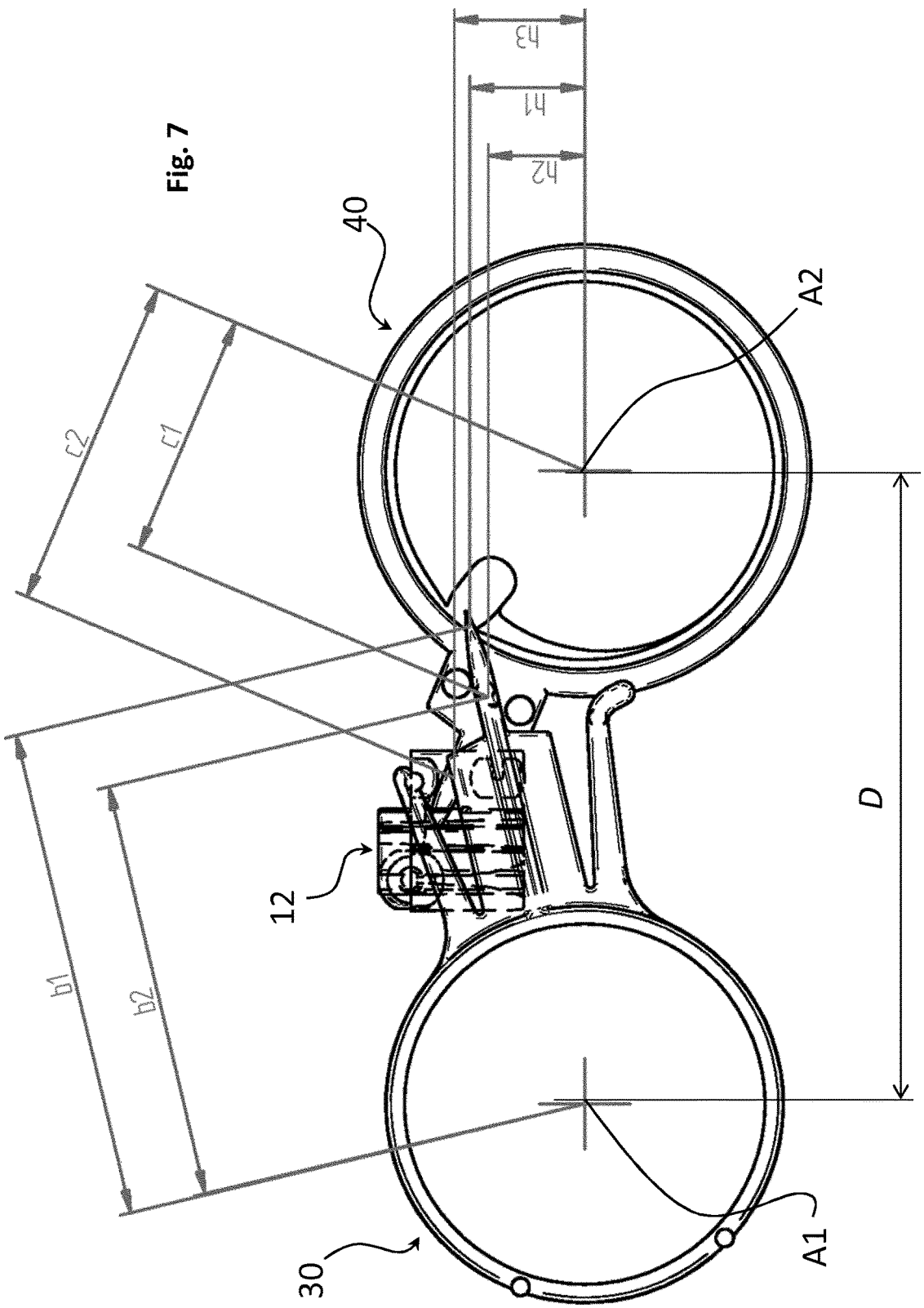

SUBCUTANEOUS DELIVERY MECHANISM FOR DRUG DELIVERY DEVICE

CROSS-REFERENCE TO RELATED APPLICATION

This application is the U.S. national stage application of International Patent Application No. PCT/EP2019/075765, filed Sep. 24, 2019.

TECHNICAL FIELD

This invention relates to a subcutaneous delivery mechanism for a drug delivery device with a needle actuation mechanism and to a drug delivery device comprising such subcutaneous delivery mechanism.

DESCRIPTION OF RELATED ART

A drug delivery device with a needle actuation mechanism is described in WO2015015379. The needle actuation mechanism in the drug delivery device described in the aforementioned document advantageously provides a reliable and safe needle actuation mechanism that can be actuated by a pump drive and that does not require overcoming high spring forces of a pre-stressed spring, or a complex mechanism for engagement and retraction of the needle.

Nevertheless a drawback of the aforementioned needle actuation mechanism in certain applications is that the lever arm requires a certain size for efficient operation. For very small drug delivery devices such as small patch devices, in particular for drugs that are pumped in very small quantities such as concentrated insulin, the aforementioned mechanism is not sufficiently compact.

It would therefore be advantageous to benefit from the advantages of a simple and reliable needle actuation mechanism yet provide this in a particularly compact configuration without reducing the distance between a retracted position and an extended delivery position of the needle.

SUMMARY OF THE INVENTION

In view of the foregoing, an object of the invention is to provide a drug delivery device with a needle actuation mechanism that is compact, safe, and reliable.

It is advantageous to provide a drug delivery device that is economical to produce.

It is advantageous to provide a drug delivery device that is comfortable to wear and easy to use.

Objects of the invention have been achieved by providing a subcutaneous delivery mechanism for a drug delivery device according to claim 1.

Disclosed herein is a subcutaneous delivery mechanism for a drug delivery device, comprising a housing, a needle holder movably mounted in the housing, a needle fixed to the needle holder, and a needle actuation mechanism configured to move the needle holder between a retracted position and an extended delivery position relative to the housing. The needle actuation mechanism comprises a first lever pivotally mounted relative to the housing and a rotary actuator rotatably mounted relative to the housing configured to engage a distal portion of the first lever to cause the first lever to rotate. The needle actuation mechanism further comprises a second lever pivotally mounted relative to the housing and coupled to the first lever such that rotation of the first lever causes rotation of the second lever in an opposite rotation direction, an engagement end of the second lever engaging the needle holder to move the needle between the retracted position and extended delivery position upon rotation of the first lever.

In an advantageous embodiment, an axis of rotation of the first lever is parallel to an axis of rotation of the second lever which is coaxial with an axis of rotation of the rotary actuator.

In an advantageous embodiment, the first lever is rotatably mounted on a first support member fixed to or integrally formed with the housing, and the second lever is rotatably mounted on a second support member, the second support member:
- fixed to or integrally formed with the housing and rotatably supporting the rotary actuator, or
- forming a portion of the rotary actuator.

In an advantageous embodiment, the first lever comprises a pivot portion pivotally mounted around a first support member, and an arm extending from the pivot portion to an engagement end, the rotary actuator comprising a catch configured to engage said engagement end of the first lever.

In an advantageous embodiment, the second lever comprises a pivot portion pivotally mounted around a second support member, and an arm extending from the pivot portion to an engagement end coupled to a coupling portion of the needle holder.

In an advantageous embodiment, the coupling portion of the needle holder is in the form of a slot receiving the engagement end of the second lever therein.

In an advantageous embodiment, an engagement end of the first lever engages a coupling interface on the second lever, the coupling interface positioned proximal a pivot portion of the second lever, distal from an engagement end of the second lever.

In an advantageous embodiment, the coupling interface comprises:
- an axially extending slot formed on the second lever insertably receiving the first lever engagement end therein; or
- an axially extending protuberance formed on the second lever insertably received in a slot formed in a portion of the first lever engagement end.

In an advantageous embodiment, the needle holder is positioned between the first and second support members.

Also disclosed herein is a drug delivery device comprising a delivery unit configured to receive a drug cartridge containing a drug to be administered to a patient in need thereof, the delivery unit further comprising the subcutaneous delivery mechanism as set forth in any of the above embodiments.

In an embodiment, the housing comprises a base wall, a needle holder guide upstanding from the base wall, the needle holder of the subcutaneous delivery mechanism comprising a guide member slidably coupled to the needle holder guide.

Further objects and advantageous features of the invention will be apparent from the claims, from the detailed description, and annexed drawings, in which:

BRIEF DESCRIPTION OF THE DRAWINGS

FIG. 1*a* is a perspective view of an embodiment of a drug delivery device according to the invention;

FIG. 1*b* is a perspective exploded view of the device of FIG. 1*a*;

FIG. 3a is a front view of FIG. 2a;

FIG. 3b is a front view of FIG. 2b;

FIG. 4a is a top view of FIG. 2a;

FIG. 6a is a front view of FIG. 5a;

FIG. 7 is a schematic view illustrating relative dimensions of levers of a subcutaneous delivery mechanism according to an embodiment of the invention.

DETAILED DESCRIPTION OF EXEMPLARY EMBODIMENTS

Figure 2A:
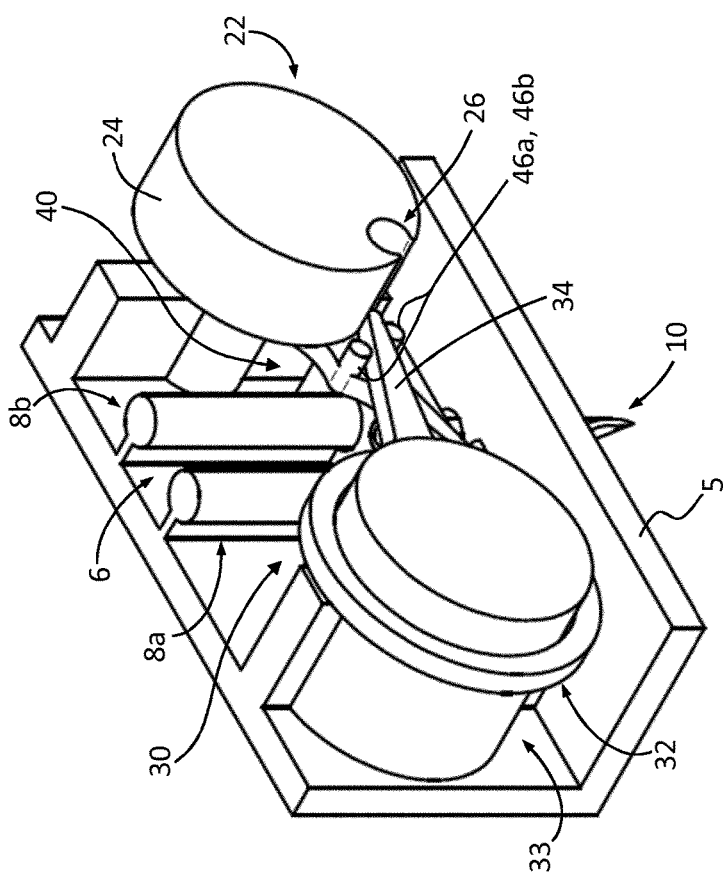
FIG. 2a is a perspective view of an embodiment of a subcutaneous delivery mechanism according to the invention, when the needle is in a retracted position.
Figure 2B:
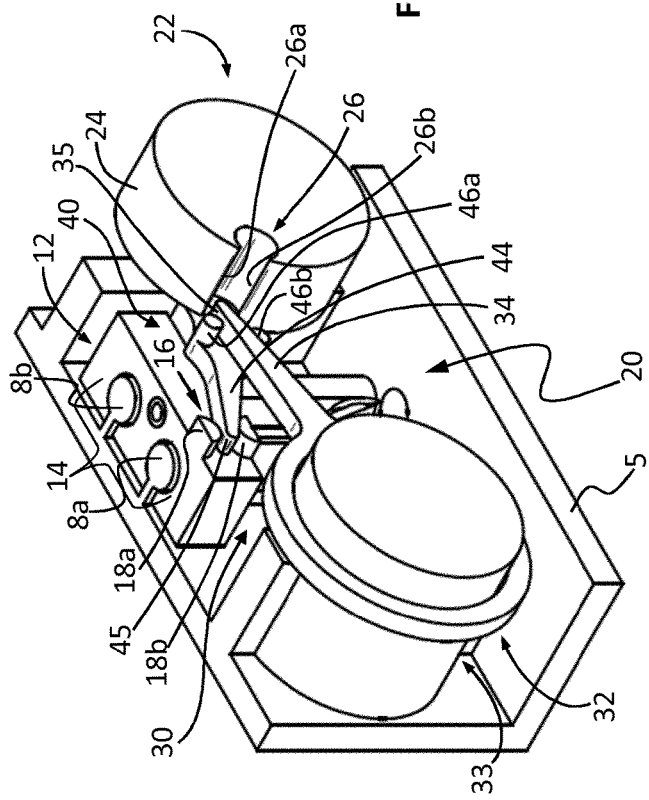
FIG. 2b is a view similar to FIG. 1a, when the needle is in an extended delivery position.
Figure 4A:
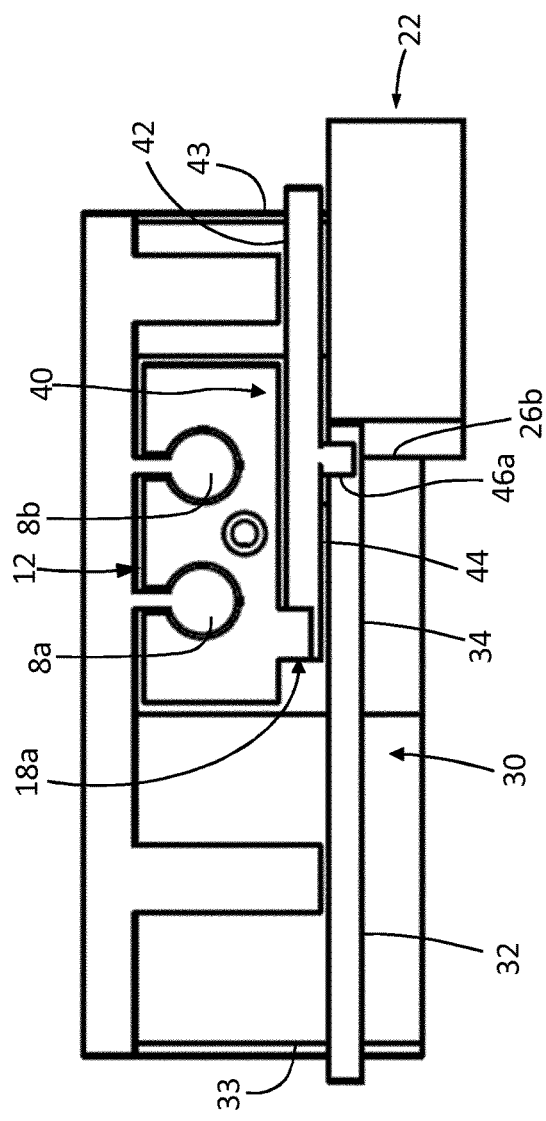
Figure 4B:
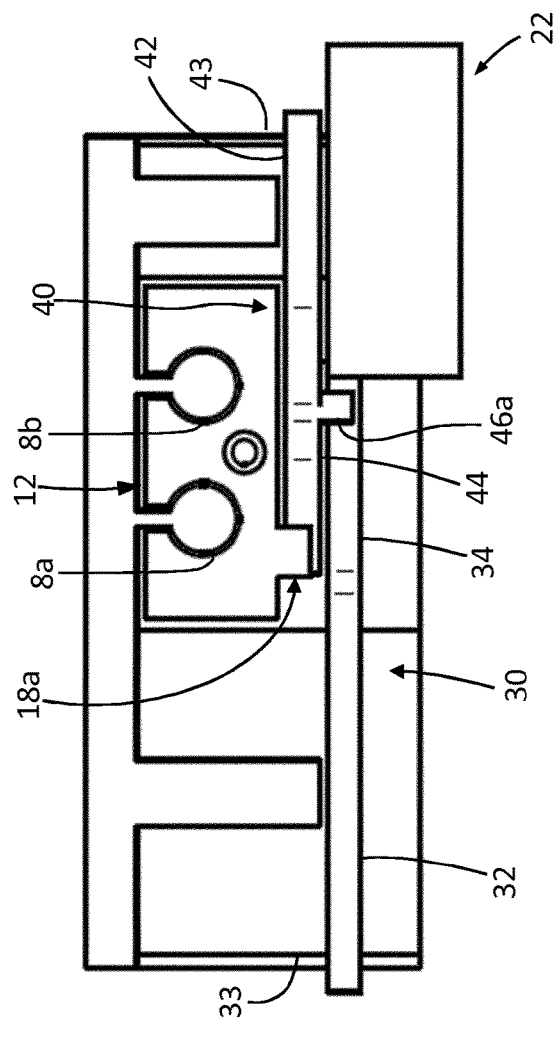
FIG. 4b is a top view of FIG. 2b.
Figure 5A:
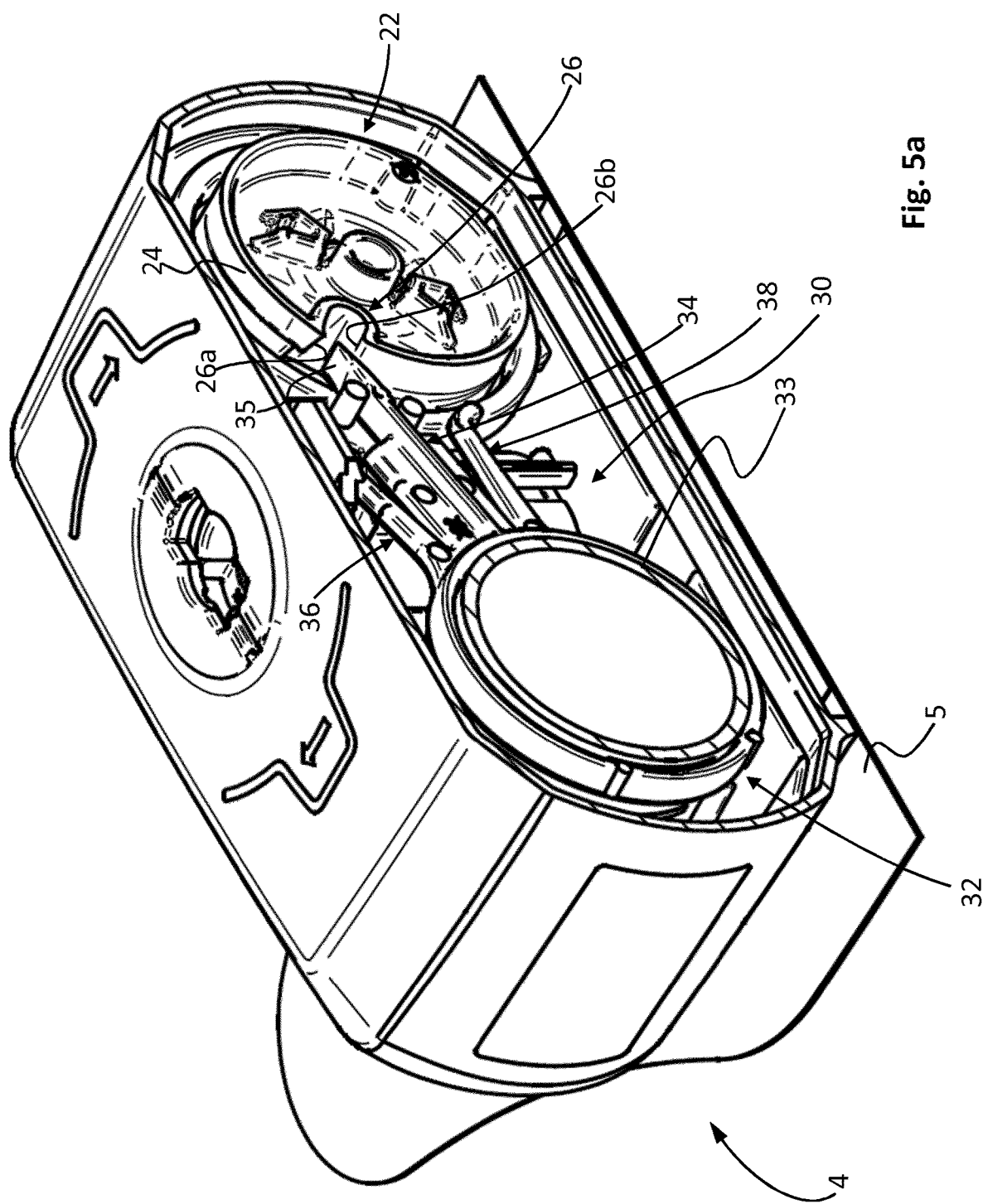
FIG. 5a is a perspective view of another embodiment of a subcutaneous delivery mechanism according to the invention, when the needle is in a retracted position.
Figure 5B:
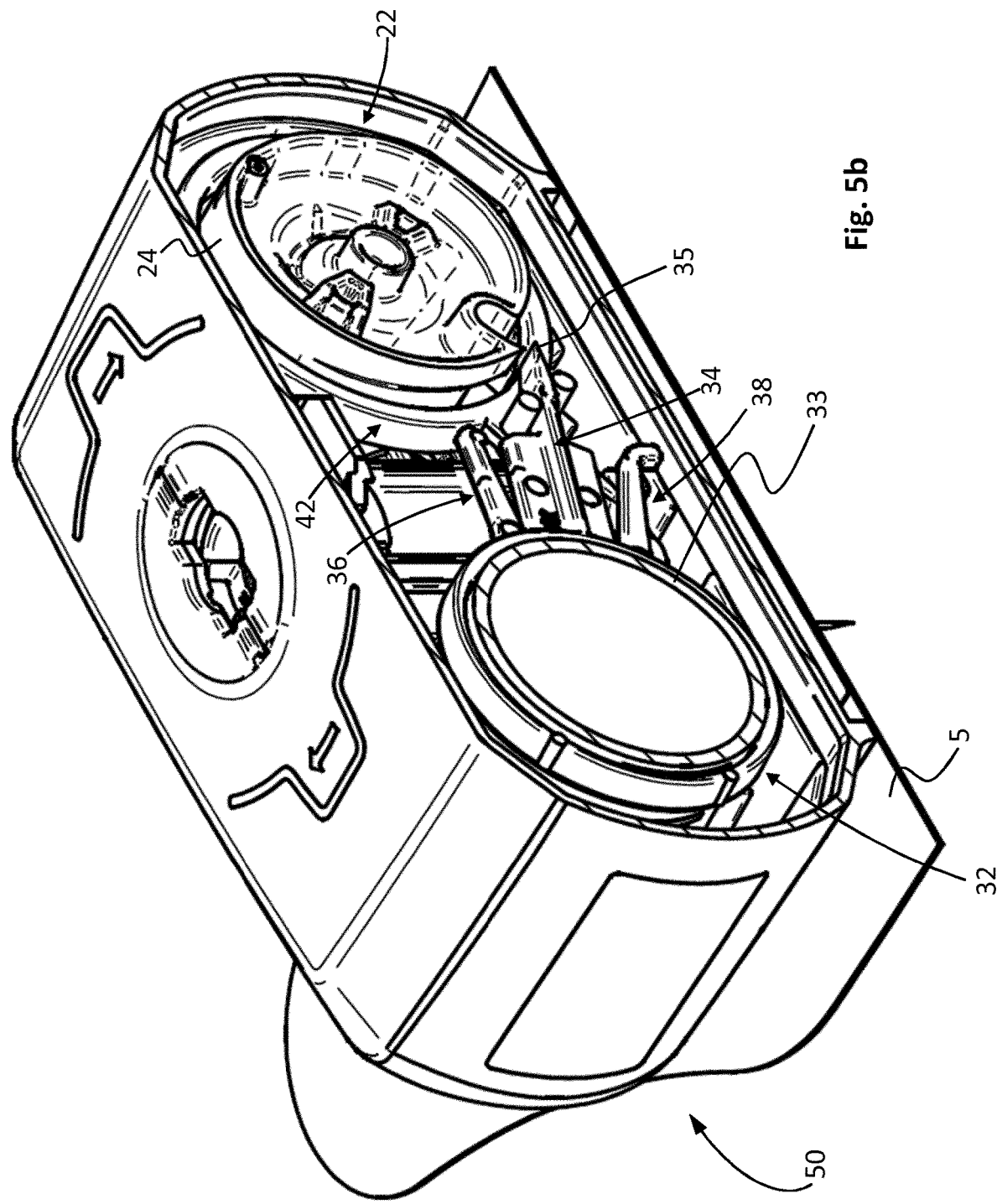
FIG. 5b is a view similar to FIG. 5a, when the needle is in an extended delivery position.

Referring to the figures, and in particular to FIGS. 1a,1b, a drug delivery device 1 comprises a delivery unit 2 and a base unit 4. In an embodiment, the delivery unit 2 is a disposable unit 2 and is removably connected to the base unit 4 which may be re-usable, although it will be appreciated that in other embodiments the base may be formed with the delivery unit as a single disposable unit.

The drug delivery device may in an embodiment be a patch pump device, with an adhesive base covered by a peel away film 9 prior to use, for mounting on a patient's skin. The adhesive base may advantageously be provided on a housing part 7 of the disposable delivery unit 2.

The delivery unit 2 comprises a subcutaneous delivery mechanism to deliver a fluid trans-dermally, a drug cartridge 3 with a reservoir containing the fluid to be administered to a patient, a pump 5 to transfer the fluid from the reservoir to the subcutaneous delivery mechanism, and a support member or housing 7 for supporting the aforementioned components.

The base unit 4 may comprise control a pump drive, control electronics and a power supply (battery). The pump drive comprises an interface that couples to a pump 5 of the delivery unit to provide the mechanical power to drive the pump 5.

The subcutaneous delivery mechanism comprises a needle actuation mechanism 20 configured to cooperate with a needle holder 12 to move a needle 10, connected to the needle holder 12, from a retracted position to an extended delivery position.

The needle actuation mechanism 20 comprises a rotary actuator 22, a first lever 30 pivotally mounted relative to the housing 7, and a second lever 40 pivotally mounted relative to the housing 7.

The first lever 30 may in an embodiment be pivotally mounted on a first support member 33 that may be fixedly connected or integrally formed with the housing 7, and the second lever 40 may be pivotally mounted on a second support member 43 that may be fixedly connected or integrally formed with the housing 7.

In variants, either or both of the first and second support members 33, 43 may be rotatably connected with the housing 7 about the axis of rotation of the respective levers. Since the levers 30, 40 rotate relative to the housing, they may rotate on a fixed support or on a support that also rotates relative to the housing. For instance, the second support member may be formed by a portion of the rotary actuator 22.

In a preferred embodiment, the axis of rotation A1 of the first lever 30 is parallel to the axis of rotation A2 of the second lever 40 which is coaxial with the axis of rotation of the rotary actuator. It may however be noted that in a variant, the second lever may be pivotally mounted around an axis that is not coaxial with the rotary actuator 22.

The device according to the invention incorporates a second lever to amplify the movement of the needle holder in comparison to a system with a single lever. As illustrated in FIG. 7, the second lever 40 engages the first lever 30 at a distance c1 and the needle holder is coupled to the second lever at a distance c2 from the rotation axis A2 of the second lever. The translation displacement of the needle holder 12 is h3, which is defined by the displacement h2 of the first lever 30. The travel in translation of the needle holder 12 can be described by $h3=h2*(c2/c1)$. The travel h2 can be approximated using the intercept theorem: $h2=h1*(b2/b1)$, where b1 is the distance from the first rotation axis A1 to the engagement of the arm 34 with the rotary actuator 22 and b2 is the distance from the first rotation axis A1 to the engagement of the arm 34 with the second lever 40. Replacing h2, the travel of the needle holder is $h3=h1*(b2/b1)*(c2/c1)$.

The parameters b1, b2, c1 and c2 are constrained by the overall size of the system. In particular:

$b2+c1\sim=D1$ (where D1 is the distance between the rotational axes A1, A2 of both levers 30. 40)

$c2+R\_fix<D1$ (where R_fix is the radius of the fixture of the first lever)

$b2+R\_act<D2$ (where R_act is the radius of the rotary actuator and D2 is the distance between the rotational axis of the first lever and the rotational axis of the rotary actuator)

$b1+R\_act=D2$

The first lever 30 comprises a pivot portion 32 mounted on the first support member 33, and an arm 34 extending therefrom to an engagement end 35. The second lever 40 comprises a pivot portion 42 mounted on the second support member 43 and an arm 44 extending therefrom to an engagement end 45. The second lever 40 further comprises a coupling interface 46 on the arm 44 of the second lever for engaging the engagement end 35 of the first lever 30 such that rotation of the first lever 30 in a first rotation direction causes rotation of the second lever 40 in a second rotation direction opposite the first rotation direction.

The coupling interface 46 may have different configurations to achieve the pivot coupling function between the two arms 34, 44. The coupling interface and the arm of the second lever may for example form an integral part and may comprise a first and a second extension 46a, 46b protruding axially from the arm 34 of the first lever 30 to form a slot therebetween, in which the engagement end 35 of the second lever is inserted. In a variant (not shown) the arm 34 of the first lever may comprise axial extensions forming a groove or slot receiving a portion of the second lever therein. The first and second levers 30, 40 may comprise various other complementary coupling interface portions configured to impart rotation of the second lever when the first lever is rotated by the rotary actuator 22, for instance an axially extending pin on one of the first and second levers received in a slot on the other of the first and second levers.

The pivot portion 32 of the first lever 30 may for instance be a ring-shaped pivot portion mounted around a first cylindrical support member 33. The pivot portion 42 of the second lever 40 may also be a ring-shaped pivot portion mounted around a second cylindrical support member 43 adjacent a side of the rotary actuator 22. Alternatively, the ring-shaped pivot portion 42 of the second lever 40 may be mounted around the circumferential outer rim 18 of the rotary actuator 22.

Figure 6B:
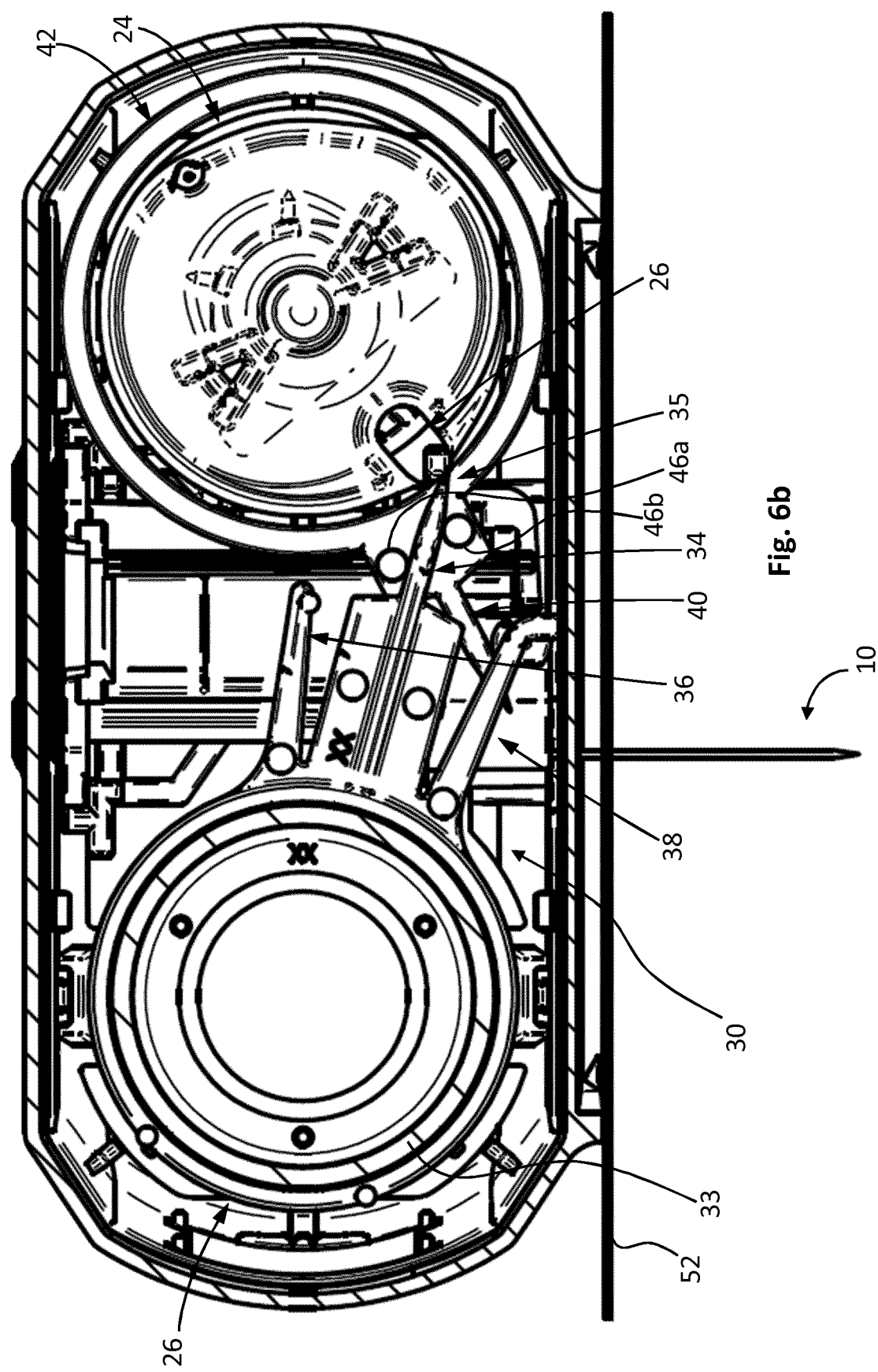
FIG. 6b is a front view of FIG. 5b.

The rotary actuator 22, which in the illustrated embodiment is essentially in the form of a disc or wheel with a circumferential outer rim 24, is provided with a catch 26 that engages an engagement end 35 of the first lever 30 when the rotary actuator 22 is rotated. The catch 26 is formed by a recess or notch in the outer rim 24 thus presenting catch edges 26a, 26b which engage respectively an upper surface and lower surface of the engagement end 35 the first lever 30. The engagement end 35 in the retracted and extended positions as shown in FIGS. 3a and 3b (one embodiment) and in FIGS. 6a, 6b (another embodiment) extends into the notch 26.

As best seen in FIGS. 5a, 5b, 6a and 6b, the first lever 30 may be configured to be in constant mechanical contact with the rotary actuator 22 and with a certain force. This contact may be maintained during the operational life of the delivery unit 2. For this purpose, the first lever 30 may for instance be provided with a first spring arm 36 and a second spring arm 38 located on each side of the engagement portion 34 of the first lever 30.

It will be appreciated however that the rotary actuator 22 may have various other forms and shapes providing an element that pushes down on the first lever 30 when moving from the retracted to extended position, respectively having an element that engages the lever 30 to move the lever upwards from the extended to the retracted positions, and the engagement end 35 may also have various shapes and forms complementary to the catch 26 of the rotary actuator 22 for effecting the aforementioned movements.

In a preferred embodiment, the rotary actuator 22 may be coupled or integrally formed with a rotor portion of a rotary pump engine. A suitable pump engine and drive unit that may advantageously be used with the present invention is described in WO 2005/039674, which is incorporated herein by reference. Thus, actuation of the needle from the retracted position to the extended delivery position, may be performed by rotating the pump rotor in the pumping direction upon initial use of the drug delivery device, and retraction of the needle at the end of use of the drug delivery device can be performed by reversing the direction of the pump rotor.

However, it will be appreciated that other rotary pump engines and pump drives may be used. Moreover, the rotary actuator may be driven by a drive that is independent of the drug delivery pump, or coupled to the pump drive via a transmission with a clutch mechanism and/or a reduction gear set.

The needle holder 12 comprises a guide member 14 that is slidably mounted on a needle holder guide 6 mounted on a base wall 5 of the housing 7 of the delivery unit 2. The needle holder guide 6 is positioned between the first and second support members 33, 43 of the needle actuation mechanism 20. The needle holder guide 6 may be for example a linear guide for translation movement therealong of the needle holder 12 to translate the needle 10 from the retracted position to an extended delivery position.

In an embodiment, the needle holder guide 6 may comprise two translation guide rails 8a, 8b while the needle holder 12 comprises a guide member 14 which may comprise two guide rails receiving apertures in which the two translation guide rails 8a, 8b pass through for translation displacement of the needle holder therealong. The needle holder 12 also comprises a coupling portion 16 which is coupled to an engagement end 45 of the arm 44 of the second lever 40.

The coupling portion 16 may have different configurations to achieve the coupling function. For example, the coupling portion 16 of the needle holder 12 comprises a first and a second extension 18a, 18b extending perpendicularly to the axis of translation of the needle holder 12 on both sides of the engagement end 45 of the arm 44 of the second lever 40. Other coupling configurations may be implemented. For example, the engagement end 45 of the arm 44 may comprise a through-hole or a hook pivotally connected to a stud connected to the needle holder 12.

When the needle 10 of the subcutaneous delivery mechanism 20 is in a retracted position, the needle holder 12 is positioned on an upper portion of the needle holder guide 6. Upon rotation of the rotary actuator 22 of the needle actuation mechanism 20 in a rotation direction to move the needle 10 from the retracted position to the extended delivery position, the first lever 30 engages the catch 26. At this point, the upper catch edge 26a pushes against the upper surface of the engagement end 35, thereby rotating the first lever 30 which causes rotation of the second lever 40. As the engagement end 45 is coupled to the needle holder 12, rotation of the second lever 40 moves the needle holder 12 from the upper portion to a lower portion of the needle holder guide 6 corresponding respectively to the retracted position and the extended delivery position of the needle 10.

In the illustrated embodiment, in the extended delivery position, the rotary actuator 22 may continue rotating in the delivery direction. In the delivery direction the upper catch edge 26a of the catch 26 is configured to be able to move past the engagement end 35 of the first lever 30 such that the rotary actuator 22 may turn in the delivery direction continuously once the needle is the extended position without being blocked by the first lever 30.

Once use of the delivery unit is finished, a command for retraction of the needle from the extended delivery position to the retracted position is executed. During this operation, the drive unit of the pump engine (not shown) is controlled to move in a reverse direction whereby the rotary actuator 22 moves in the reverse direction. In the reverse direction, a lower catch edge 26b of the catch 26 engages the engagement end 35 of the first lever 30 thus lifting it up. As the upper side of the arm 34 is in contact with the first extension 46a of the coupling interface 46, the second lever 40 is lifted up by the first lever, thus moving up the needle holder 12 so as to move the needle 10 from the extended to the retracted position.

The needle actuation mechanism according to embodiments of the invention advantageously provides a very compact needle actuation mechanism, and thus a compact subcutaneous delivery mechanism, while ensuring a large distance of travel of the needle between a retracted position and an extended delivery position necessary to achieve optimal subcutaneous penetration for drug delivery. Moreover, the needle actuation mechanism according to embodiments of the invention is simple, robust and reliable.

LIST OF FEATURES ILLUSTRATED

Drug delivery device 1
  Delivery unit 2 (disposable part)
    Drug cartridge 3
    Housing 7
      Base wall 5
      Needle holder guide 6

Translation guide rails 8a, 8b
First support member 33
Second support member 43
Subcutaneous delivery mechanism
  Needle 10
  Needle holder 12
    Guide member 14
      Guide rails receiving apertures
    Coupling portion 16
      First extension 18a
      Second extension 18b
  Needle actuation mechanism 20
    Rotary actuator 22
      Rim 24
      Catch 26
        Recess/notch
        Catch edges
        Upper catch edge 26a
        Lower catch edge 26b
        Coupling interface
    First lever 30
      Pivot portion 32
      Arm 34
      Engagement end 35
        First spring arm 36 (one embodiment)
        Second spring arm 38 (one embodiment)
    Second lever 40
      Pivot portion 42
      Arm 44
      Engagement end 45
      First lever coupling interface 46
        First extension 46a
        Second extension 46b
Base unit 4 (reusable part)
  Electronic control system
  Power source (battery)
  Pump drive
    Coupling interface

The invention claimed is:

1. A subcutaneous delivery mechanism for a drug delivery device, comprising a housing, a needle holder movably mounted in the housing, a needle fixed to the needle holder, and a needle actuation mechanism configured to move the needle holder between a retracted position and an extended delivery position relative to the housing, the needle actuation mechanism comprising a first lever pivotally mounted relative to the housing and a rotary actuator rotatably mounted relative to the housing configured to engage a distal portion of the first lever to cause the first lever to rotate, wherein the needle actuation mechanism further comprises a second lever pivotally mounted relative to the housing and coupled to the first lever such that rotation of the first lever causes rotation of the second lever in an opposite rotation direction, an engagement end of the second lever engaging the needle holder to move the needle between the retracted position and extended delivery position upon rotation of the first lever.

2. The subcutaneous delivery mechanism according to claim 1, wherein an axis of rotation (A1) of the first lever is parallel to an axis of rotation (A2) of the second lever.

3. The subcutaneous delivery mechanism according to claim 2, wherein the axis of rotation (A2) of the second lever is coaxial with an axis of rotation of the rotary actuator.

4. The subcutaneous delivery mechanism according to claim 1, wherein the first lever is rotatably mounted on a first support member fixed to or integrally formed with the housing, and the second lever is rotatably mounted on a second support member, the second support member:
    fixed to or integrally formed with the housing and rotatably supporting the rotary actuator, or
    forming a portion of the rotary actuator.

5. The subcutaneous delivery mechanism according to claim 1, wherein the first lever comprises a pivot portion pivotally mounted around a first support member, and an arm extending from the pivot portion to an engagement end, the rotary actuator comprising a catch configured to engage said engagement end of the first lever.

6. The subcutaneous delivery mechanism according to claim 1, wherein the second lever comprises a pivot portion pivotally mounted around a second support member, and an arm extending from the pivot portion to an engagement end coupled to a coupling portion of the needle holder.

7. The subcutaneous delivery mechanism according to claim 6, wherein the coupling portion of the needle holder comprising a slot receiving the engagement end of the second lever therein.

8. The subcutaneous delivery mechanism according to claim 1, wherein an engagement end of the first lever engages a coupling interface on the second lever, the coupling interface positioned proximal a pivot portion of the second lever, distal from an engagement end of the second lever.

9. The subcutaneous delivery mechanism according to claim 8, wherein the coupling interface comprises:
    an axially extending slot formed on the second lever insertably receiving the first lever engagement end therein; or
    an axially extending protuberance formed on the second lever insertably received in a slot formed in a portion of the first lever engagement end.

10. The subcutaneous delivery mechanism according to claim 1, wherein the needle holder is positioned between the first and second support members.

11. A drug delivery device comprising a delivery unit configured to receive a drug cartridge containing a drug to be administered to a patient in need thereof, the delivery unit further comprising the subcutaneous delivery mechanism according to claim 1.

12. The drug delivery device according to claim 11, wherein the housing comprises a base wall, a needle holder guide upstanding from the base wall, the needle holder of the subcutaneous delivery mechanism comprising a guide member slidably coupled to the needle holder guide.

* * * * *